United States Patent [19]

Falk

[11] Patent Number: 4,944,093
[45] Date of Patent: Jul. 31, 1990

[54] FORCEPS WITH SHEARING JAWS

[75] Inventor: Ernst Falk, Sternenfels-Diefenbach, Fed. Rep. of Germany

[73] Assignee: Richard Wolf GmbH, Fed. Rep. of Germany

[21] Appl. No.: 261,487

[22] Filed: Oct. 24, 1988

[30] Foreign Application Priority Data

Oct. 26, 1987 [DE] Fed. Rep. of Germany ....... 3736150

[51] Int. Cl.⁵ .............................................. B23P 19/02
[52] U.S. Cl. .................................... 30/251; 606/174; 606/205
[58] Field of Search ...................... 128/321, 305, 751; 606/174, 205, 207; 30/245, 246, 249, 250, 251; 294/104

[56] References Cited

U.S. PATENT DOCUMENTS

| 3,585,985 | 6/1971 | Gould | 128/321 X |
| 4,569,131 | 2/1986 | Falk et al. | 30/251 |
| 4,785,825 | 11/1988 | Romaniuk et al. | 128/321 X |

FOREIGN PATENT DOCUMENTS

| 245402 | 4/1912 | Fed. Rep. of Germany | 128/305 |
| 8316034.5 | 11/1983 | Fed. Rep. of Germany | . |
| 382369 | 11/1964 | Switzerland | 128/346 |

Primary Examiner—Michael H. Thaler
Attorney, Agent, or Firm—Hill, Van Santen, Steadman & Simpson

[57] ABSTRACT

A forceps and in particular hooked shears, has a distal extremity of the forceps shaft provided with a recess of the one fixed branch of the forceps jaws, with which branch there co-operates a double-armed pivotally displaceable jaw branch by means of a scissors grip and a push and pull rod. The recess of the fixed jaw branch is continued by a shaft slot whereof the delimiting edge forms a stop for a stepped surface of the push and pull rod placed in impingement in the closed position of the jaws and the open position of the jaws is restricted by impingement of a surface of the pivotable jaw branch against the top distal edge of the push rod.

1 Claim, 1 Drawing Sheet

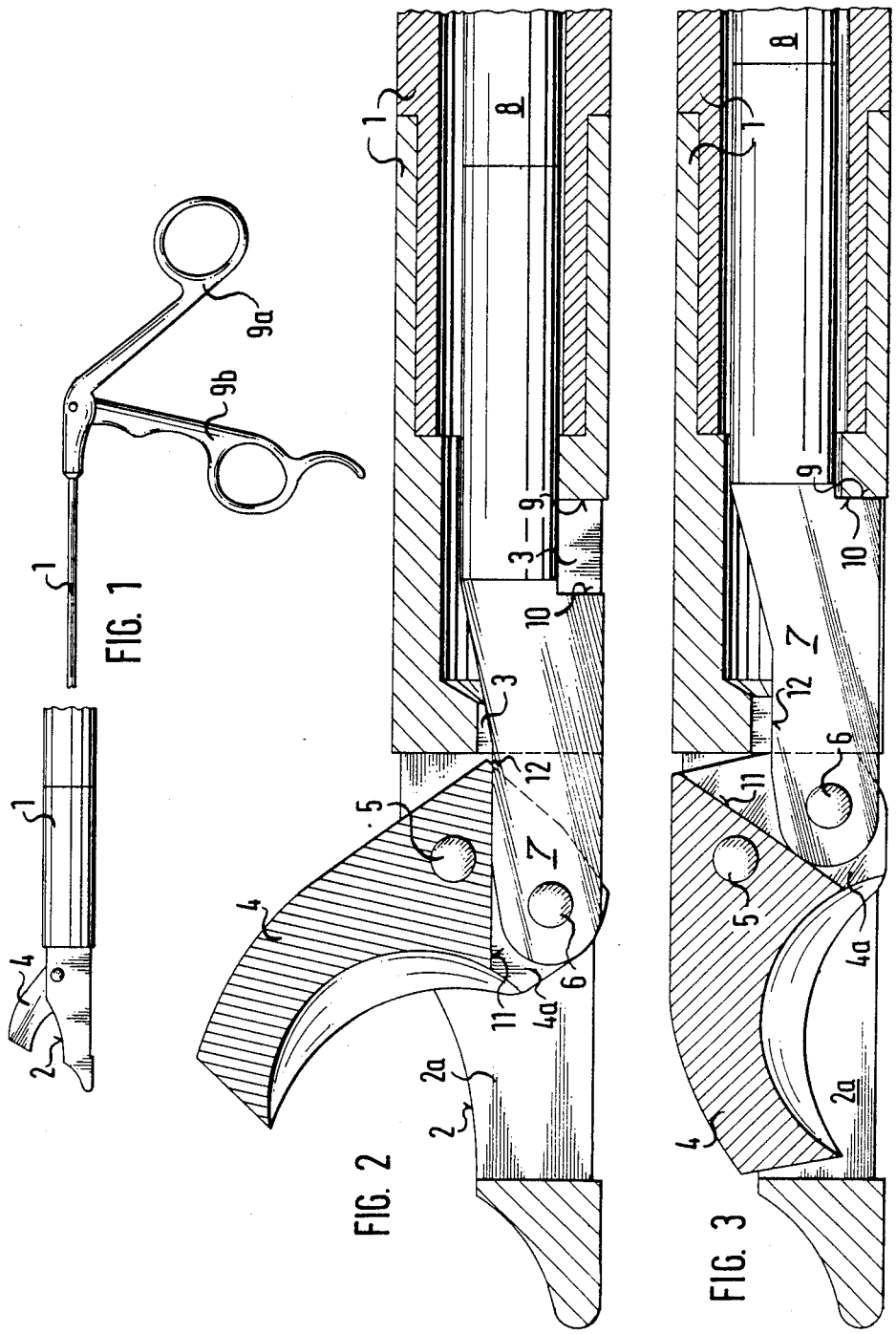

FORCEPS WITH SHEARING JAWS

BACKGROUND OF THE INVENTION (a) Field of the Invention

This invention relates to a pair of forceps, in particular being a hooked or curved trimmer or the like and having forceps jaws arranged on the distal end of a shaft. A stationary branch or jaw is formed by the distal end of a shaft which is provided with a recess, and the other double-armed jaw branch is pivotable by means of a scissors grip and a coupled push and pull rod around a transverse spindle or pin with the open and closed positions of the forceps jaws being determined by means of stops.

(b) Description of the Prior Art

Such hooked trimmers or shears are as described in the DE-GM 83 16 034, and comprise one fixed and one movable branch of the forceps jaws, which are constructed in such manner that the closed position and the open position are delimited by stops on the push and pull rod operating the pivotable jaw branch which stops impinge against fixed stops in the two terminal positions of the pivotable jaw branch.

Stops of this nature are usable only if the forceps and its shaft diameter have sufficiently large dimensions, since the stops then provide a reliable delimitation for the open and closed positions of the forceps jaws.

SUMMARY OF THE INVENTION

The main object of the invention consists in dimensioning, positioning and structurally forming the stops in such manner for forceps or hooked shears of larger as well as minimal measurements, in particular with shaft diameters of between say 1.5 and 2.5 mm, that they ensure reliable delimitation of the open and closed positions of the forceps jaws.

The present invention consists in a forceps, in particular, hooked shears or the like, comprising forceps jaws situated at the distal extremity of a shaft, whereof a stationary branch is formed by the distal extremity of the shaft which is provided with a recess and whereof theother double-armed jaw branch is pivotable around a transverse spindle by means of a scissors grip and a coupled push and pull rod with the open and closed positions of the forceps jaws being determined by means of stops, characterized in that in the closed position of the forceps jaws, a bottom step of the pull or traction rod bears against the proximal delimiting edge of a lower longitudinal slot of said shaft and in that, in the open position, a proximally situated end side or edge of the pivotable jaw branch bears against the upper edge on the distal extremity of the push rod.

Preferably, the shaft is provided along the axial length of the jaws with a recess traversing the same from top to bottom intended for the pivotable jaw branch, a bottom shaft slot continuing the shaft recess receives a flattened distal extension of the pull rod which in jointed manner connects the bottom extension acting as a stop and having a stepped surface with the proximal arm of the pivotable jaw branch.

The external diameter of the shaft may amount to between 1.5 and 2.5 mms.

In a preferred embodiment, the distal shaft recess forming the fixed branch of the forceps jaws and the flat extension of the push rod are produced by application of the sparking wire erosion method, and the longitudinal slot in continuation of the recess of the shaft is produced by the attritional erosion method.

Since the stops are situated in the region of the forceps jaws section and thanks to their structural form, these stops are very stable even in the case of minimal diametrical shear sizes and thus form a reliable delimitation for the terminal positions of the pivotable jaw branch, without the patient being unintentionally injured in or damaging the forceps jaw branch.

BRIEF DESCRIPTION OF THE DRAWINGS

In order that the invention may be more readily understood, and embodiment thereof will now be described, by way of example, with reference to the accompanying drawings, in which:

FIG. 1 is a side elevational view of a forceps hooked shear or trimmer, with the distal extremity enlarged, FIG. 2 is an enlarged longitudinal cross-sectional through the distal extremity of the forceps shear according to FIG. 1, with the forceps jaws opened, and FIG. 3 is a longitudinal cross-section corresponding to FIG. 2, with the forceps jaw closed.

DESCRIPTION OF THE PREFERRED EMBODIMENT

Referring to the drawings, there is shown a forceps or hooked shears comprising a hollow shaft 1 having a distal excision or recess 2a forming the stationary cutting branch 2 of the forceps jaws, which is followed at the proximal side by a lower longitudinal slot 3 of the shaft. The movable, double-armed, jaw branch 4a is pivotally journalled around a transverse pin 5 in the recess 2a. To this end, a transverse pin 6 of the jaw arm 4 is acted upon by the extremity 7 of a push and pull rod 8 which is longitudinally displaceable in the hollow shaft 1 by means of the forceps handle 9b which is movable with respect to the forceps handle 9a rigidly joined to the shaft 1, for displacement of the jaws branch 4. The push rod 8 acts with its distal extremity 7 which is a flat-structure part on the branch arm 4a at 6, and the part 7 is guided in the shaft slot 3. The connection of the parts 7 and 8 or other parts is established by laser beam welding. With this proximal terminal edge, the shaft slot 3 forms a stop 9 and the flat push rod portion is provided with a stepped surface 10 by means of a bottom step, which in the closed position of the forceps jaws (FIG. 3) is placed in parallel contact with the stop surface 9, in such manner that the pivotal displacement of the jaw branch 4, together with the positioning of its cutting edge, is always delimited within the area of the recess 2a.

In the open position of the forceps jaws according to FIG. 2, a proximal base surface 11 of a bifurcated recess of the jaw branch 4a is stopped by impingement against the distal top edge 12 of the flat distal extension 7.

If the spatial shapes and dimensions of the forceps or hooked shears are such that the shaft diameter lies between 1.5 and 2.5 mms, the recess 2a and the flat distal extension 7 of the push rod 8 may be produced by means of the spark wire erosion method, whereas the longitudinal slot 3 for the guiding of the flat push rod extremity 7 as well as the bifurcated recess of the jaw arm 4a are produced by an attritional erosion method, in which connection the bifurcated recess may nevertheless also be produced by cutting, machining or in particular by means of a sawing operation. Thanks to this method, the two stop surfaces 9 and 10 may be produced in perfectly planoparallel manner, so that neither a one-sided attrition can occur on these surfaces, nor a positional change of the jaw branch 4 when the forceps jaws are closed.

Whilst the invention has been particularly described it will be appreciated that it is not limited thereto but includes all modifications and variations falling within its scope.

What is claimed is:

1. A forceps, in particular shears, comprising a tubular shaft having a recess transversing a distal end of the shaft from top to bottom to form a stationary shearing jaw, a scissors grip being mounted at a proximal end of the shaft, a push and pull rod extending in said shaft having a proximal end connected to a movable handle of the scissors grip, a movable shearing jaw being mounted on the stationary jaw by a transverse spindle for pivotable movement, said movable jaw being pivotably connected to a distal end of the push and pull rod to move between a closed position received in said recess and an opened position as said movable handle is moved, first stop means for defining the closed position comprising a step on the push and pull rod engaging an edge provided on said shaft adjacent the distal end thereof, and second stop means for defining the opened position comprising a stop edge on said movable jaw coating with a stop surface on said push and pull rod, said recess having a bottom portion extending proximally from the spindle to form a bottom shaft slot having a proximal edge forming said edge on said shaft of the first stop means, said push and pull rod having a flattened distal extension received in said slot, said step being provided on said extension and said stop surface being formed by an upper edge of said extension, said movable jaw at a proximal end having a bifurcating recess receiving a distal end of the flattened distal extension of the push and pull rod, said bifurcating recess having a base surface forming said stop edge of the movable jaw.

* * * * *